(12) United States Patent
Won et al.

(10) Patent No.: US 8,846,630 B2
(45) Date of Patent: Sep. 30, 2014

(54) PHARMACEUTICAL COMPOSITION FOR TREATING CANCER

(75) Inventors: Misun Won, Daejeon (KR); Kyung-Sook Chung, Daejeon (KR); Young Joo Kim, Daejeon (KR); Hye Kyung Hong, Busan (KR); Young Il Yeom, Daejeon (KR); Chae Ok Yun, Seoul (KR); Yu-Kyoung Oh, Seoul (KR); Kyung Bin Song, Daejeon (KR); Hee Gu Lee, Daejeon (KR); Eun Young Song, Seoul (KR); Seok Hoon Song, legal representative, Seoul (KR); Young Ho Kim, Seoul (KR); Moon Hee Kim, Seoul (KR); Kyeong-Eun Jung, Anyang-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/512,583

(22) PCT Filed: Nov. 1, 2010

(86) PCT No.: PCT/KR2010/007600
§ 371 (c)(1),
(2), (4) Date: Oct. 5, 2012

(87) PCT Pub. No.: WO2011/065677
PCT Pub. Date: Jun. 3, 2011

(65) Prior Publication Data
US 2013/0028957 A1 Jan. 31, 2013

(30) Foreign Application Priority Data
Nov. 30, 2009 (KR) ........................ 10-2009-0116727

(51) Int. Cl.
 C12N 15/11 (2006.01)
 C07H 21/04 (2006.01)
 A61K 31/711 (2006.01)
 A61K 31/713 (2006.01)
 A61K 31/7105 (2006.01)

(52) U.S. Cl.
 CPC ............. *A61K 31/711* (2013.01); *A61K 31/713* (2013.01); *A61K 31/7105* (2013.01)
 USPC ........................................ 514/44 A; 536/24.5

(58) Field of Classification Search
 USPC ........................................ 514/44 A; 536/24.5
 See application file for complete search history.

(56) References Cited

U.S. PATENT DOCUMENTS

| 8,090,542 | B2 * | 1/2012 | Khvorova et al. ............... 702/20 |
| 2004/0086884 | A1 | 5/2004 | Beach et al. ..................... 514/44 |
| 2004/0106567 | A1 | 6/2004 | Hagstrom et al. ............... 514/44 |
| 2006/0035815 | A1 | 2/2006 | Chen et al. ....................... 514/44 |
| 2008/0113351 | A1 | 5/2008 | Naito et al. ...................... 514/44 |
| 2011/0008370 | A1 | 1/2011 | Won et al. ................... 424/174.1 |
| 2011/0054005 | A1 | 3/2011 | Naito et al. ...................... 514/44 |

FOREIGN PATENT DOCUMENTS

| EP | 1752536 | 2/2007 |
| KR | 10-2008-0044909 | 5/2008 |
| KR | 10-0883471 | 2/2009 |
| KR | 10-2009-0060183 | 6/2009 |
| WO | WO 2005/116204 | 12/2005 |
| WO | WO 2007/021142 | 2/2007 |
| WO | WO 2008/156012 | 12/2008 |

OTHER PUBLICATIONS

Letter/Written Disclosure of the Information Disclosure Statement for the above-referenced application, mailed on Aug. 21, 2012, 2 pages.
Alvarez et al., "RNA interference-mediated silencing of the respiratory syncytial virus nucleocapsid defines a potent antiviral strategy," Antimicrob Agents Chemother. 53(9):3952-3962. (2009).
Chiu, Y. and R. Rana, "siRNA function in RNAi: a chemical modification analysis, " RNA. 9(9):1034-1048 (2003).
Crooke, S., "Progress in antisense technology: the end of the beginning," Methods Enzymol. 313:3-45 (2000).
Derwent English abstract for WO 2008/156012, published Dec. 24, 2008, entitled: "Novel mortalin short interference RNA or short hairpin RNA, useful as anticancer agent," Dialog File No. 351, Accession Nbr. 18611074, 6 pages.
GenBank Accession No. NM_145018, "*Homo sapiens* chromosome 11 open reading frame 82 (C11orf82), mRNA," Apr. 1, 2012 [online], [retrieved on May 25, 2012]. Retrieved from the Internet<URL:ncbi.nlm.nih.gov/nuccore/NM_145018 [3 pages].
Henschel et al., "DEQOR: a web-based tool for the design and quality control of siRNAs," Nucleic Acids Res. 32(Web Server issue):W113-W120 (2004).
Jackson et al., "Position-specific chemical modification of siRNAs reduces "off-target" transcript silencing," RNA.12(7):1197-1205 (2006).

(Continued)

*Primary Examiner* — Jon E Angell
(74) *Attorney, Agent, or Firm* — McKenna Long & Aldridge LLP; Stephanie Seidman

(57) ABSTRACT

The present invention provides a pharmaceutical composition for treating cancer, comprising at least one selected from deoxyribonucleic acids (DNA) for encoding small interfering RNA (siRNA) which complementarily binds to the base sequence of the transcript (mRNA transcript) of the FLJ25416 gene, represented by sequence number 3, sequence number 5, and sequence number 7 to inhibit the intracellular expression of the FLJ25416 gene, antisense RNA which inhibits expression of the FLJ25416 gene, and short hairpin RNA (shRNA) which inhibits expression of the FLJ25416 gene. As the siRNA, which is complementary to the base sequence of the transcript (mRNA transcript) of the FLJ25416 gene, the antisense RNA, and the shRNA, according to the present invention, inhibit expression of the FLJ25416 gene which is known to be expressed in cancer cells, and thus kill cancer cells, the composition of the present invention can be used as a novel anti-cancer agent.

6 Claims, 6 Drawing Sheets

(56) References Cited

OTHER PUBLICATIONS

Kubo et al., "Modified 27-nt dsRNAs with dramatically enhanced stability in serum and long-term RNAi activity," Oligonucleotides. 17(4):445-464 (2007).
Kurreck, J., "Antisense technologies. Improvement through novel chemical modifications," Eur J Biochem. 270(8):1628-1644 (2003).
Rana, T., "Illuminating the silence: understanding the structure and function of small RNAs," Nat Rev Mol Cell Biol. 8(1):23-36 (2007).
Soutschek et al., "Therapeutic silencing of an endogenous gene by systemic administration of modified siRNAs," Nature 432(7014):173-178 (2004).
International Search Report, issued Aug. 18, 2011 in connection with International Patent Application No. PCT/KR2010/007600, 2 pages.
Letter/Written Disclosure of the Information Disclosure Statement for the above-referencedd application, mailed on Aug. 2, 2013, 2 pages.
Chang et al., "MMP13 is potentially a new tumor marker for breast cancer diagnosis." Oncol Rep. 22(5):1119-1127 (2009).
Cho et al., "Upregulation of Bcl-2 is associated with cisplatin-resistance via inhibition of Bax translocation in human bladder cancer cells." Cancer Lett. 237(1):56-66 (2006).
English language abstract of Korean Patent Publication No. KR 10-2009-0083804 (Korean Patent Application No. KR 10-2008-0009813), published Aug. 4, 2009, Korean Intellectual Property Office, 2 pages.
Kim, Y., "Computational siRNA design considering alternative splicing," Methods Mol Biol. 623:81-92 (2010).
Park et al., "AsiDesigner: exon-based siRNA design server considering alternative splicing," Nucleic Acids Res. 36(Web Server issue):W97-W103 (2008).
Translation of International Preliminary Report on Patentability, issued Jun. 12, 2012, in connection with corresponding International Patent Application No. PCT/KR2010/007600, 7 pages.
Letter/Written Disclosure of the Information Disclosure Statement for the above-referenced application, mailed on Sep. 4, 2012, 2 pages.

* cited by examiner

SEQUENCE LISTING

```
<160> NUMBER OF SEQ ID NOS: 30

<210> SEQ ID NO 1
<211> LENGTH: 19
<212> TYPE: DNA
<213> ORGANISM: Homo sapiens

<400> SEQUENCE: 1
cagaacagaa agtccatct                                                19

<210> SEQ ID NO 2
<211> LENGTH: 19
<212> TYPE: DNA
<213> ORGANISM: Homo sapiens

<400> SEQUENCE: 2
gatacaactc agaatctat                                                19

<210> SEQ ID NO 3
<211> LENGTH: 19
<212> TYPE: DNA
<213> ORGANISM: Homo sapiens

<400> SEQUENCE: 3
gattcatgga gccttgttt                                                19

<210> SEQ ID NO 4
<211> LENGTH: 19
<212> TYPE: DNA
<213> ORGANISM: Homo sapiens

<400> SEQUENCE: 4
gtcatcatga aattggagt                                                19

<210> SEQ ID NO 5
<211> LENGTH: 19
<212> TYPE: DNA
<213> ORGANISM: Homo sapiens
```

-continued

<400> SEQUENCE: 5
ctatcatttc cctgatcaa                                                19

<210> SEQ ID NO 6
<211> LENGTH: 19
<212> TYPE: DNA
<213> ORGANISM: Homo sapiens

<400> SEQUENCE: 6
agtagaggct gtctctgta                                                19

<210> SEQ ID NO 7
<211> LENGTH: 19
<212> TYPE: DNA
<213> ORGANISM: Homo sapiens

<400> SEQUENCE: 7
cagaagagat ctgcatgtt                                                19

<210> SEQ ID NO 8
<211> LENGTH: 19
<212> TYPE: DNA
<213> ORGANISM: Homo sapiens

<400> SEQUENCE: 8
ccactggttt gcacaggta                                                19

<210> SEQ ID NO 9
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 9
cagaacagaa aguccaucu                                                19

<210> SEQ ID NO 10
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 10
agauggacuu ucguucug                                                 19

<210> SEQ ID NO 11
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 11
gauacaacuc agaaucuau                                                19

<210> SEQ ID NO 12
<211> LENGTH: 19
<212> TYPE: RNA
<213> ORGANISM: Artificial Sequence
<220> FEATURE:
<223> OTHER INFORMATION: siRNA for FLJ25416, antisense

```
<400> SEQUENCE: 12
auagauucug aguuguauc                                                    19

<210> SEQ ID NO 13
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 13
gauucaugga gccuuguuu                                                    19

<210> SEQ ID NO 14
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 14
aaacaaggcu ccaugaauc                                                    19

<210> SEQ ID NO 15
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 15
gucaucauga aauuggagu                                                    19

<210> SEQ ID NO 16
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 16
acuccaauuu caugaugac                                                    19

<210> SEQ ID NO 17
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 17
cuaucauuuc ccugaucaa                                                    19

<210> SEQ ID NO 18
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 18
uugaucaggg aaaugauag                                                    19
```

```
<210> SEQ ID NO 19
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 19
aguagaggcu gucucugua                                                      19

<210> SEQ ID NO 20
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 20
uacagagaca gccucuacu                                                      19

<210> SEQ ID NO 21
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 21
cagaagagau cugcauguu                                                      19

<210> SEQ ID NO 22
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 22
aacaugcaga ucucuucug                                                      19

<210> SEQ ID NO 23
<211> LENGTH: 19
<212> TYPE: RNA
<213> ORGANISM: Artificial Sequence
<220> FEATURE:
<223> OTHER INFORMATION: siRNA for FLJ25416, sense

<400> SEQUENCE: 23
ccacugguuu gcacaggua                                                      19

<210> SEQ ID NO 24
<211> LENGTH: 19
<212> TYPE: RNA
<213> ORGANISM: Artificial Sequence
<220> FEATURE:
<223> OTHER INFORMATION: siRNA for FLJ25416, antisense

<400> SEQUENCE: 24
uaccugugca aaccagugg                                                      19

<210> SEQ ID NO 25
<211> LENGTH: 18
<212> TYPE: RNA
<213> ORGANISM: Artificial Sequence
<220> FEATURE:
<223> OTHER INFORMATION: scrambled siRNA, sense
```

```
<400> SEQUENCE: 25
cuacgccacc aauuucgu                                                  18

<210> SEQ ID NO 26
<211> LENGTH: 18
<212> TYPE: RNA
<213> ORGANISM: Artificial Sequence
<220> FEATURE:
<223> OTHER INFORMATION: scrambled siRNA, antisense

<400> SEQUENCE: 26
acgaaauugg uggcguag                                                  18

<210> SEQ ID NO 27
<211> LENGTH: 2997
<212> TYPE: DNA
<213> ORGANISM: Homo sapiens

<400> SEQUENCE: 27
atgaacagaa gacgaaaatt tcttctagcc tcagtacttg ctctccagaa ttcaagtttt      60
atatatccat catgtcagaa gtgcttctct aggataatcc tggtctccaa aaggtctaat     120
tgtccaaaat gtggctctac tggtgaatct ggaaatgcca attacagata caaactttcc     180
ttaaaagttg cagaatcaaa caaattgttt gttattactg tatttggaag ttgcttagat     240 acatttttg gtcttactgc cactggtttg cacaggtaca ttcaggatcc taataaaatt      300
ccagaaacac tggacaatga tacaactcag aatctattaa ctaaagcagt tgaaacttgc     360
tttgttggac aaagctttat ttttggagtg acgaattttg aaaaccaacc tggacaaggt     420
tcagatgcca gtaacttctt acagcaatgc tctgaccaca aagaaaagc caaagcacta     480 gtggcttgcc agattgttct accagaccca ggtattgcag gctttactgt cattgactac     540
ttccatcaac tttttgcagac ttttaatttc aggaaacttc agtgtgactc tcaggcacct     600
aacaatcact tacttgcttt agatcactca aatagtgatc tcagcagcat atatacttct     660
gacagcactt ctgatttttt caagtcctgc agcaaggata ctttttcaaa attctggcag     720
ccatcacttg aattcacttg cattgtttca caactaacag ataatgatga ttttcagct     780 tcagaacaaa gtaaggcctt tggtactctt cagcagaaca gaaagtccat ctccattgca     840
gaggccactg gttccagtag ctgccatgat cccattcagg attcatggag ccttgtttca     900
tatatggata aaagagtac agcagaaaag ttgggtaaag aacttggctt acaagctaag     960
gagctgagtg cagttcacag cagtcatcat gaaattggag ttaatgactc taatttattc    1020
tctttggaaa tgcgagagcc ccttgagtca agtaatacaa aatccttcca cagtgcagtg    1080
gaaattaaaa ataggtccca gcatgagcta ccatgttttc agcatcatgg tatagatacc    1140
ccaactagcc ttcagaagag atctgcatgt tgtccacctt cgttactcag acttgaagag    1200
acagccagca gttcccagga tggtgaccct caaatttggg atgatctgcc attctctgaa    1260
agcctgaaca agtttctggc agttcttgaa agtgagattc tgtaaccca ggcagatgtc     1320 agtagtagga acatcatgt agataatgac attgataaat tcatgcaga ccacagcagg      1380 ttatctgtga ctccccagag aactactgga gccctgcata caccacctat agctttaaga    1440
tcatcacaag taatagtcaa agcaaactgt agcaaagatg acttccttt caactgtaaa     1500 ggaaatctaa gtcctagtgt tgaaaaggag tcaacaccag ataacaaagt agaggctgtc    1560
tctgtaaatc ataatggaag agatatgtca gaatattttt taccgaatcc ttacctgtca    1620
gctctgtctt catcttcaaa agatttagaa acaatagtta ctcttaagaa gactatcaga   1680
```

| | | | | |
|---|---|---|---|---|
| atctcaccac | acagggagag | tgaccattct | agtctaaata | acaaatattt gaatggatgt | 1740 |
| ggagaaatat | cagtttcaga | aatgaatgaa | aagttgacaa | ctctgtgtta taggaagtat | 1800 |
| aatgatgtct | ctgatctttg | caaattagaa | aataaacaat | attgtaggtg gtccaagaac | 1860 |
| caagatgaca | gttttacaat | ttgcaggaaa | cttacatatc | ctttagaaac tctttgcaat | 1920 |
| agtccaaata | gaagtacaaa | tacattgaaa | gaaatgcctt | ggggacatat caataacaac | 1980 |
| gtaacacaga | gctattctat | tggttatgaa | ggtagctatg | atgcctctgc tgatctcttt | 2040 |
| gatgatattg | ctaaagaaat | ggacattgca | actgagatta | ccaaaaaatc acaggatatt | 2100 |
| ttgttaaaat | ggggaacatc | tttggcagaa | agtcacccett | cagagtctga tttttcactg | 2160 |
| agatcacttt | ctgaagactt | catccagcct | tcacaaaaat | tatccttgca aagcctatct | 2220 |
| gactctaggc | attcaagaac | atgctctcca | acacctcatt | ttcaatcaga ttcagaatat | 2280 |
| aattttgaaa | atagtcaaga | ctttgttcca | tgttcacagt | caactccaat ttcagggttc | 2340 |
| caccaaacaa | gaattcatgg | gataaacaga | gctttcaaaa | aacctgtatt ttattcagat | 2400 |
| cttgatggta | actatgaaaa | aataaggatt | ttccctgaaa | atgacaaaca gcaagccagc | 2460 |
| ccaagctgtc | caaaaaatat | aaaaacacct | agccagaaaa | tcagaagccc tattgtatct | 2520 |
| ggtgtttcac | aaccagacgt | tttcaatcac | tacccttttg | ctgagtgcca tgaaactgat | 2580 |
| agtgatgaat | gggtccctcc | taccacacaa | aaaatatttc | cttcagatat gcttggattc | 2640 |
| caaggcatag | gtctagggaa | atgccttgct | gcctatcatt | tccctgatca acaagagtta | 2700 |
| ccaagaaaga | aactgaaaca | tattagacaa | ggaaccaata | aaggtttaat taagaagaaa | 2760 |
| ttaaagaata | tgcttgcagc | agttgttacg | aaaaagaaaa | ctcataaata taactgtaaa | 2820 |
| agttcaggct | ggatttccaa | atgtccagac | attcaagtct | tagcagcacc tcagctgcac | 2880 |
| cctattcttg | gacctgattc | ttgttcagaa | gtcaaatgtt | gccttccatt ttcagaaaaa | 2940 |
| ggcccacctt | cagtgtgtga | aactcgaagt | gcttggtcac | ctgaattgtt ttcataa | 2997 |

```
<210> SEQ ID NO 28
<211> LENGTH: 44
<212> TYPE: DNA
<213> ORGANISM: Artificial Sequence
<220> FEATURE:
<223> OTHER INFORMATION: shRNA for FLJ25416

<400> SEQUENCE: 28
gattcatgga gccttgtttg agctcaaaca aggctccatg aatc                    44

<210> SEQ ID NO 29
<211> LENGTH: 44
<212> TYPE: DNA
<213> ORGANISM: Artificial Sequence
<220> FEATURE:
<223> OTHER INFORMATION: shRNA for FLJ25416

<400> SEQUENCE: 29
ctatcatttc cctgatcaag agctcttgat cagggaaatg atag                    44

<210> SEQ ID NO 30
<211> LENGTH: 44
<212> TYPE: DNA
<213> ORGANISM: Artificial Sequence
<220> FEATURE:
<223> OTHER INFORMATION: shRNA for FLJ25416
```

-continued

```
<400> SEQUENCE: 30
cagaagagat ctgcatgttg agctcaacat gcagatctct tctg                         44
```

PHARMACEUTICAL COMPOSITION FOR TREATING CANCER

RELATED APPLICATIONS

This application is the National Stage of International Application No. PCT/KR2010/007600, filed Nov. 1, 2010, which claims benefit of priority to Korean Application No. 10-2009-0116727, to Mi Sun Won, Kyung Sook Chung, Young Joo Kim, Hye Kyung Hong, Young Il Yeom, Chae Ok Yun, Yu Kyung Oh, Kyung Bin Song, Hee Gu Lee, Eun Young Song, Young Ho Kim, Moon Hee Kim and Kyeong Eun Jung, entitled "PHARMACEUTICAL COMPOSITION CONTAINING DNA ENCODING siRNA, ANTISENSE RNA, OR shRNA WHICH SUPPRESSES FLJ25416 EXPRESSION FOR TREATING CANCER," filed Nov. 30, 2009.

TECHNICAL FIELD

The present invention relates to a pharmaceutical composition for treating cancer, comprising an siRNA (small interfering RNA), an antisense RNA and/or a DNA (deoxyribonucleic acid) coding for an shRNA (short hairpin RNA), all the RNAs being inhibitory of the intracellular expression of FLJ25416 by complimentarily binding to the transcript (mRNA) of the FLJ25316 gene.

BACKGROUND ART

Recently, the FLJ25416 gene (NCBI GenBank Access No. NM_145018), encoding the hypothetical protein FLJ25416, was known to be associated with cancer (Korean Patent Laid-Open Publication No. 10-2009-0060183).

RNA interference (RNAi) is a process which regulates the expression of genes of interest at a post-transcriptional level as siRNA specifically binds to mRNA transcripts and induces their degradation. Recently, RNAi has become prominent as a solution to problems with the development of conventional chemically synthesized medicines. Able to selectively regulate the expression of proteins of interest at a post-transcriptional level, RNAi is utilized in the development of therapeutics for various diseases, particularly, tumors. Generally, small molecule chemical drugs optimized for targeting proteins of interest are not developed without a long period of time and a great deal of expense. In contrast, siRNA medicines based on RNAi allows the rapid development of leading compounds optimized for all protein targets including non-druggable targets, which is one of the greatest advantages of the siRNA medicines. Whereas it difficulty is put into the production of protein or antibody drugs because of their complicated processes, siRNA is relatively easy to produce on a mass scale thanks to the easiness of its synthesis and isolation. Further, small nucleic acid molecules such as siRNA have an advantage over protein drugs because such nucleic acids are more stable. In addition, in contrast to conventional drugs, small RNA molecules such as siRNA perform only antagonistic actions on specific target molecules.

The first consideration of therapy with small nucleic acid molecules, such as siRNA, is to select an optimal sequence associated with activity from among the target base sequence. Certain binding sites of target transcripts are known to have the greatest influence on the efficiency of RNAi. A database accumulated over the last few years provides algorithms that allow the design of the sequences of siRNA that regulate the expression of target mRNA. In practice, however, all of the siRNAs constructed by the computational In-Silico design cannot effectively regulate the expression of target RNA within cells or in vivo. Even though the siRNA satisfies the requirement of the complimentary binding with target transcripts, it is known that there are various and still unidentified factors that are involved in determining the efficacy of RNAi, including stability between ribonucleic acids and proteins, intracellular location of ribonucleic acids, the state of the proteins implicated in RNAi, etc. There is therefore a need for a technique by which a candidate group consisting of various target sequences on one gene transcript is set and the optimal member of the candidate group that is the most suitable for use in the interference is selected.

DISCLOSURE

Technical Problem

It is an object of the present invention to provide an siRNA (small interfering RNA), an antisense RNA and a DNA (deoxyribonucleic acid) coding for an shRNA (short hairpin RNA), all RNAs being suppressive of the intracellular expression of FLJ25416 by complementarily binding to an FLJ25416 transcript (mRNA), and a pharmaceutical composition for the therapy of cancer, comprising the siRNA, the antisense RNA and/or the DNA coding for an shRNA.

Technical Solution

In accordance with one aspect thereof, the present invention provides a pharmaceutical composition for the therapy of cancer, comprising a nucleic acid molecule selected from the group consisting of an siRNA (small interfering ribonucleic acid), an antisense ribonucleic acid, a DNA encoding an shRNA (short hairpin ribonucleic acid), and a combination thereof, all of the RNAs being suppressive of the expression of FLJ25416 within cells by complementarily binding to a base sequence of the FLJ25416 transcript (mRNA) represented by SEQ ID NO: 3, SEQ ID NO: 5 or SEQ ID NO: 7.

The siRNA used in the composition of the present invention may be one species which can bind only to one selective sequence of the FLJ25416 transcript (mRNA) or may be two or more different species which can target the FLJ25416 transcript at two or more sequence positions.

In one preferred embodiment, the siRNA is selected from the group consisting of siRNA having the sense sequence set forth as SEQ ID NO: 13 and the antisense sequence set forth as SEQ ID NO: 14, siRNA having the sense sequence set forth as SEQ ID NO: 17 and the antisense sequence set forth as SEQ ID NO: 18, siRNA having the sense sequence set forth as SEQ ID NO: 21 and the antisense sequence set forth as SEQ ID NO: 22, and a combination thereof.

As used herein, the term "siRNA" is intended to include siRNA that becomes resistant to enzymatic degradation of nucleases by structural modification. Persons skilled in the art can synthesize and modify siRNA in a desired fashion using a method known in the art (refer to Andreas Henschel, Frank Buchholzl and Bianca Habermann (2004) DEQOR: a web-based tool for the design and quality control of siRNAs. Nucleic Acids Research 32(Web Server Issue): W113-W120). Although the double-helical structure of siRNA is more stable than the single helical structure of RNA or antisense oligonucleotides, siRNA is susceptible to nuclease activity. Structural modification may make siRNA less susceptible to nuclease degradation. Structural modifications that make siRNA stable and resistant to nuclease degradation are well known to those skilled in the art.

The siRNA useful in the present invention may undergo a structural modification. Preferably, the modification of the siRNA may be selected from among 2'-O-methyl modification, 2'-F modification, amino modification, cholesterol conjugation, and a combination thereof.

As used herein, the term "2'-O-methyl modification" means that a methoxy group is substituted for the hydroxyl group at position 2' on the ribose moiety. The term "2'-F modification" means that a fluorine atom is substituted for the hydroxyl group at position 2' on the ribose moiety. By "amino modification" is meant the modification of a substitute a hexylamino group for the 5' hydroxyl group on the sense strand of siRNA. The term "cholesterol conjugation," as used herein, means the modification adapted to conjugate cholesterol to the 5'-end of the sense strand of siRNA. These modifications have been engineered to provide siRNAs with increased stability to nucleases and enhanced affinity for target mRNA. In addition, the modifications are found to enhance the intracellular uptake of siRNA and to reduce the immune response of siRNA (refer to RNA 2006, 12, pi 197, RNA 2003, 9, p 1034, AAC 2009, 53, p 3952, Nature 2004, 432, p 173, Oligonucleotides 2007, 17, p 445).

When their structures are modified chemically as stated above, the ribonucleic acids shows increased stability and resistance to nuclease activity and are improved in pharmacokinetic profile such as retention time and efficacy, in vivo.

The antisense RNA used in the composition of the present invention may be one species which can bind only to one selective sequence of the FLJ25416 transcript (mRNA) or may be two or more different species which can target the FLJ25416 transcript at two or more sequence positions.

In one preferred embodiment, the antisense RNA has at least one nucleotide sequence selected from the group consisting of those set forth as SEQ ID NOS: 14, 18 and 22.

The term "antisense RNA," as used herein, refers to a single-stranded RNA that is complementary to a gene transcript (mRNA). Antisense oligonucleotides have been suggested to regulate the expression of proteins at a transcriptional, translational or splicing level by binding to DNA or RNA targets coding for the proteins. The antisense RNA useful in the present invention may be structurally modified to have improved resistance to nucleases in vivo. Persons skilled in the art can synthesize and modify siRNA in a desired fashion using a method known in the art (refer to European Journal of Biochemistry. 2003; 270: 1628-1644. Methods Enzymol. 2000: 313, 3-45).

As for the DNA coding for shRNA, it may be one species coding for one shRNA which can bind only to one selective sequence of the FLJ25416 transcript (mRNA) or may be two or more different species coding for respective shRNAs, which can target the FLJ25416 transcript at two or more sequence positions.

In one preferred embodiment of the present invention, the DNA has at least one selected from the group consisting of nucleotide sequences set forth as SEQ ID NOS: 28, 29 and 30 which respectively encode shRNAs having a set of nucleotide sequences of SEQ ID NOS: 13 and 14, a set of nucleotide sequences of SEQ ID NOS: 17 and 18, and a set of nucleotide sequences of SEQ ID NOS: 21 and 22.

As used herein, the term "shRNA" is a sequence of single-stranded RNA which is typically 45 to 70 nt long and makes a tight hairpin turn that can be used to silence target gene expression by means of RNAi. For RNAi, shRNA is processed into functional siRNA by dicer. DNA encoding an shRNA molecule is designed to have a sense sequence and an antisense sequence of siRNA with a 3-10-mer linker (loop sequence) present therebetween. To be used, the resulting synthesized DNA may be cloned into a plasmid vector or an shRNA molecule may be inserted into a retrovirus such as lentivirus or adenovirus.

In addition to structural modification, a safe and effective delivery system is required for improving the intracellular uptake of nucleic acids such as siRNA. In this regard, the composition may comprise a nucleic acid delivery system carrying the siRNA, the antisense RNA, the DNA and/or the shRNA encoded by the DNA.

For use in intracellular uptake of nucleic acids such as siRNA, the nucleic acid delivery system may be a viral or a non-viral vector. Most widely used are viral vectors because they exhibit high delivery efficiency and a long half life in serum. Representative among them are retroviral vectors, adenoviral vectors, and adeno-associated viral vectors. Non-viral vectors have an advantage over viral vectors in that they are of low toxicity and of low immunogenicity. In addition, they can be repetitively administered and are easy to complex with ribonucleic acids and to produce on a mass scale. Further, when conjugated with a ligand specific for diseased cells or tissues, the non-viral vector can deliver the nucleic acid substance selectively to the cells or tissues. There are various forms of non-viral vectors including liposomes, cationic polymers, micelles, emulsions, and nanoparticles. A nucleic acid delivery system can remarkably increase the intracellular uptake of a nucleic acid substance of interest and can transport the nucleic acid substance to certain animal cells depending on the purpose of the nucleic acid substance to be delivered.

The nucleic acid delivery system useful in the present invention may be selected from among a cationic liposome, a cationic polymer and a combination thereof.

If it takes the form of a cationic liposome or polymer, the nucleic acid delivery system can easily complex with nucleic acids of interest because electrostatic bonds are formed between the positive charges of the nucleic acid delivery system and the negative charges of the nucleic acids such as siRNA.

An expression vector carrying siRNA, antisense RNA or shRNA (small hairpin RNA) can be constructed using a method known in the art. For example, U.S. Patent Publication Nos. 20040106567 and 20040086884 teach delivery mechanisms based on viral vectors, non-viral vectors, liposomal delivery systems, plasmid injecting systems, artificial viral envelopes, and polylysine conjugates and provide various expression vectors.

The composition of the present invention may further comprise a pharmaceutically acceptable carrier. Examples of the pharmaceutically acceptable carrier useful in the present invention include water, saline, phosphate buffered saline, dextrin, glycerol, ethanol, and a combination thereof. The composition may be formulated into a dosage form which can release the active ingredient in a rapid or a sustained or delayed manner after administration.

For use in the therapy of cancer, the siRNA or the nucleic acid delivery system complexed with siRNA may be introduced into cells. As will be further explained in the following Example section, the siRNA introduced directly or via the nucleic acid delivery system into cells acts to suppress the expression of FLJ25416, which plays an important role in carcinogenesis, causing the death of cancer cells.

The cancer to be treated with the composition is preferably selected from among lung cancer, uterine cervical cancer, colorectal cancer, stomach cancer and liver cancer (Korean Patent Laid-Open Publication No. 10-2009-0060183).

Once introduced into cells in vivo or ex vivo, the nucleic acid substance in the composition of the present invention down-regulates the expression of the target protein FLJ25416 or repairs mutations on the target gene, thereby suppressing the growth of the cancer generated by the overexpression of FLJ25416.

In the context of the use of the siRNA, the antisense RNA, the shRNA-encoding DNA or the complex of each nucleic acid with a nucleic acid delivery system in the present invention, the term "therapeutically effective amount" means an amount sufficient to produce a desired result in cancer therapy. Therefore, the amount of the active ingredient may vary depending on various factors including the kind and severity of the disease to be treated, the kind of the nucleic acid to be administered, the kind of the formulation to be used, the patient's age, body weight, general health, gender and diet, the time of administration, the route of administration, the duration of the treatment, and other drugs used in combination or coincidentally with the composition and like factors well known in the medical arts. The composition, or the siRNA, the antisense RNA and/or the shRNA-encoding DNA may be administered intravenously, intraarterially, intramuscularly, intrathoracically, transdermally, intranasally, by inhalation, topically, rectally, orally, intraocularly, or intradermally. The composition may be administered in such an amount that the daily dose of siRNA, antisense RNA or shRNA is on the order of 0.01 ng/kg~100 mg/kg for adults.

As described below, the siRNAs of the present invention are suppressive of the expression of FLJ25416 by complimentarily binding to FLJ25416 transcripts (mRNA) having the nucleotide sequences set forth as SEQ ID NOS: 3, 5 and 7. Particularly effective among them, as will be further explained in the following Example section, are siRNAs having a set of the sense sequence of SEQ ID NO: 13, the antisense sequence of SEQ ID NO: 14, a set of the sense and the antisense sequence of SEQ ID NO: 17, the antisense sequence of SEQ ID NO: 18, a set of the sense sequence of SEQ ID NO: 21 and the antisense sequence of SEQ ID NO: 22. The antisense RNA that effectively suppresses the expression of FLJ25416 by complementarily binding to FLJ25416 transcripts (mRNA) having the nucleotide sequences set forth as SEQ ID NOS: 3, 5 and 7 were found to have the nucleotide sequence of SEQ ID NO: 14, 18 or 22. Likewise, DNA molecules having the nucleotide sequence set forth as SEQ ID NO: 28 designed to encode an shRNA comprising the nucleotide sequences of SEQ ID NOS: 13 and 14, the nucleotide sequence set forth as SEQ ID NO: 29 designed to encode an shRNA comprising the nucleotide sequences of SEQ ID NOS: 17 and 18, and the nucleotide sequence set forth as SEQ ID NO: 30 designed to encode an shRNA comprising the nucleotide sequences of SEQ ID NOS: 21 and 22 transcribe the shRNAs within cells, thus effectively downregulating the expression of FLJ25416.

Hence, in accordance with another aspect thereof, the present invention provides an siRNA molecule, having a set of the sense sequence of SEQ ID NO: 13 and the antisense sequence of SEQ ID NO: 14, which functions to suppress the expression of FLJ25416.

In accordance with a further aspect thereof, the present invention provides an siRNA molecule, having a set of the sense sequence of SEQ ID NO: 17 and the antisense sequence of SEQ ID NO: 18, which functions to suppress the expression of FLJ25416.

In accordance with still a further aspect thereof, the present invention provides an siRNA molecule, having a set of the sense sequence of SEQ ID NO: 21 and the antisense sequence of SEQ ID NO: 22, which functions to suppress the expression of FLJ25416.

In accordance with still another aspect thereof, the present invention provides an antisense RNA molecule, having the base sequence set forth as SEQ ID NO: 14, which functions to suppress the expression of FLJ25416.

In accordance with yet a further aspect thereof, the present invention provides an antisense RNA molecule, having the base sequence set forth as SEQ ID NO: 18, which functions to suppress the expression of FLJ25416.

In accordance with yet another aspect thereof, the present invention provides an antisense RNA molecule, having the base sequence set forth as SEQ ID NO: 22, which functions to suppress the expression of FLJ25416.

In accordance with an additional aspect thereof, the present invention provides a DNA molecule, having the nucleotide sequence set forth as SEQ ID NO: 28, which encodes an shRNA suppressive of the expression of FLJ25416.

In accordance with a further additional aspect thereof, the present invention provides a DNA molecule, having the nucleotide sequence set forth as SEQ ID NO: 29, which encodes an shRNA suppressive of the expression of FLJ25416.

In accordance with another additional aspect thereof, the present invention provides a DNA molecule, having the nucleotide sequence set forth as SEQ ID NO: 30, which encodes an shRNA suppressive of the expression of FLJ25416.

In one embodiment of the present invention, the siRNA may be structurally modified by 2'-O-methyl modification, 2'-F modification, amino modification or cholesterol conjugation and may be used in association with a nucleic acid delivery system.

In accordance with still a further additional aspect thereof, the present invention provides the use of the siRNA, the antisense RNA and/or the shRNA-encoding DNA in the preparation of an anticancer agent.

In accordance with still another additional aspect thereof, the present invention provides a therapeutical method for cancer, comprising introducing the siRNA, the antisense RNA, the shRNA (short hairpin RNA)-encoding DNA (deoxyribonucleic acid), the shRNA encoded by the DNA and/or the composition of the present invention into cells in a patient in need thereof.

In the present invention, the therapy of cancer is intended to include treating cancer, preventing the onset of cancer, and retarding the progress of cancer.

In the present invention, the FLJ25416 transcript has a nucleotide sequence set forth as SEQ ID NO: 27, with a mutation of at least one base by deletion, substitution and/or insertion.

Advantageous Effects

Because the siRNA, the antisense RNA and/or the shRNA are complementary enough to FLJ25416 transcripts (mRNA) that they suppress the expression of FLJ25416, a protein common to various types of cancer, by RNAi, the composition of the present invention can be very useful as an anticancer agent.

MODE FOR INVENTION

Figure 1:
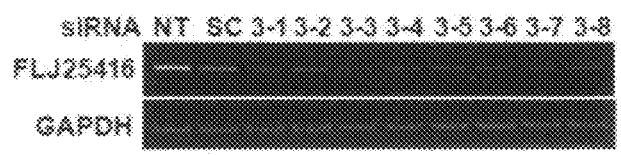
FIG. 1 is a photograph after electrophoresis was performed, showing the inhibitory effects of the siRNAs of the present invention on the expression levels of FLJ25416 transcript in lung cancer A549 cell line.

The following non-limiting Examples serve to illustrate selected embodiments of the invention. It will be appreciated that variations in proportions and alternatives in elements of the components shown will be apparent to those skilled in the art and are within the scope of embodiments of the present invention. Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

EXAMPLES

Example 1

Design of Target Nucleotide Sequence Candidates Complementary to siRNAs for Suppressing the Expression of FLJ25416

Target nucleotide sequence candidates to which siRNAs could bind were designed on the transcripts of FLJ25416.

Using an siRNA design program (algorithm disclosed in Korean Patent Application No. 10-2008-0009813 to the Korea Research Institute of Bioscience & Biotechnology (KRIBB)), target nucleotide sequences to which siRNA could bind were selected on the FLJ25416 mRNA sequence of SEQ ID NO: 27 (*Homo sapiens* chromosome 11 open reading frame 82 (C11orf82), mRNA; NCBI GenBank No. NM_145018).

Table summarizes candidates of the nucleotide sequences which siRNA can target.

TABLE 1 siRNA-Bindable Target Nucleotide Sequences of FLJ25416

| SEQ ID NO: | Sequence Position | Nucleotide Sequence |
| --- | --- | --- |
| 1 | 814-832 | cagaacagaaagtccatct |
| 2 | 319-337 | gatacaactcagaatctat |
| 3 | 880-898 | gattcatggagccttgttt |
| 4 | 983-1000 | gtcatcatgaaattggagt |
| 5 | 2673-2691 | ctatcatttccctgatcaa |
| 6 | 1548-1566 | agtagaggctgtctctgta |
| 7 | 1153-1171 | cagaagagatctgcatgtt |
| 8 | 260-278 | ccactggtttgcacaggta |

Example 2

Synthesis of siRNA Candidates Capable of Suppressing the Expression of FU25416 siRNAs having the sequences of Table 2 which were respectively adapted to bind to the 8 sequences designed in Example 1 were synthesized in Samchully Pharmaceuticals (Seoul, Korea). Each of the synthesized siRNA molecules had a duplex form consisting of a 19-mer sense and a 19-mer antisense strand, with two bases (TT) suspended from the 3'-end of each strand. Synthesis cycles of deblocking, coupling, oxidation and capping were performed on a solid phase support to afford the RNA of the desired length. For this, an automatic synthesizer (Polygene DNA/RNA Synthesizer) was used. After completion of the synthesis, the synthesized oligonucleotides were separated from the solid phase resin by heating in a mixture of ammonia and ethanol (3:1) and deprotected. The solution was concentrated, followed by the deprotection of the 2'-TBDMS group by TBAF. HPLC purification separated RNA molecules. MALDI-TOF mass spectrometry was performed to examine whether their nucleotide sequences were coincident with the desired sequences. Then, the sense strands were allowed to hybridize with corresponding antisense strands to produce duplex siRNAs. Separately, siScram (scrambled siRNA) was synthesized for use as a negative control in a similar manner. The siScram is an siRNA which shares no homology with human genes and thus has no influence on the proliferation of human cells. Nucleotide sequences of the 8 siRNA candidates and the siScram are given in Tables 2 and 3, respectively.

TABLE 2 siRNA Candidates for Suppressing the
Expression of FLJ25416

| Example | SEQ ID NO: | Sense Sequence (5'-3')<br>Antisense Sequence (5'-3') | Sequence Position |
|---|---|---|---|
| 2-1 | 9<br>10 | cgaacagaaaaguccauc<br>agauggacuuucuguucug | 814-832 |
| 2-2 | 11<br>12 | gauacaacucagaaucuau<br>auagauucugaguuguauc | 319-337 |
| 2-3 | 13<br>14 | gauucauggagccuuguuu<br>aaacaaggcuccaugaauc | 880-898 |
| 2-4 | 15<br>16 | gucaucaugaaauuggagu<br>acuccaauuucaugaugac | 983-1000 |
| 2-5 | 17<br>18 | cuaucauuccccugaucaa<br>uugaucagggaaaugauag | 2673-2691 |
| 2-6 | 19<br>20 | aguagaggcugucucugua<br>uacagagacagccucuacu | 1548-1566 |
| 2-7 | 21<br>22 | cagaagagaucugcauguu<br>aacaugcagaucucuucug | 1153-1171 |
| 2-8 | 23<br>24 | ccacugguuugcacaggua<br>uaccugugcaaaccagugg | 260-278 |

TABLE 3 siScram

| | SEQ ID NO: | Sense Sequence (5'-3')<br>Antisense Sequence (5'-3') |
|---|---|---|
| siScrma | 25<br>26 | cuacgccaccaauuucgu<br>acgaaauuggugggcguag |

Example 3

Preparation of Composition Comprising siRNA for Suppressing Expression of FLJ25416 and Cationic Liposome

The 8 siRNA candidates for suppressing the expression of FLJ25416, prepared in Example 2, were allowed to form complexes with a cationic liposome as a carrier.

For this, a transfection reagent composed of cationic liposomes (HiPerFect transfection Reagent QIAGEN, Netherland) was mixed with each of the 8 siRNA candidates of Example 2 for 20 min at room temperature to give compositions in which siRNAs formed a complex with the cationic liposome (3-1~3-8). Likewise, siScram was allowed to complex with the cationic liposome.

Example 4

RT-PCR Assay for Ability of the siRNA to Down-Regulate the Expression of FLJ25416 Transcript

To examine effects of the siRNA compositions on the growth of cancer cells, a reverse-transcription polymerase chain reaction assay was performed in the following procedure.

The lung cancer cell line A549 (the Korean Cell Line Bank) was grown to 70% confluency. To the lung cancer cells, the complex compositions of siRNA and cationic liposome were added in such an amount that the final concentration of siRNA in the culture medium was 50 nM. Complexes were prepared by slowly pipetting the liposome and the siRNA and leaving the mixture at room temperature for 20 min. They were plated into well plates containing the cells and incubated at 37° C. for 72 hours in a $CO_2$ incubator.

After 24 hours, total ribonucleic acid (RNA) was isolated from the cells using the Trizol reagent (Invitrogen, Carlsbad, Calif., USA) and reverse transcribed into complementary deoxyribonucleic acid (cDNA) using a one-step RT-PCR Pre-Mix kit (iNtRON Biotechnology, INC). For use in PCR, primers specific for FLJ25416 were 5-cagaagccctattg-tatctgg-3 (N-terminal primer), 5-cttgcagcagttgttgttacgaa-3 (C-terminal primer).

Figure 2:
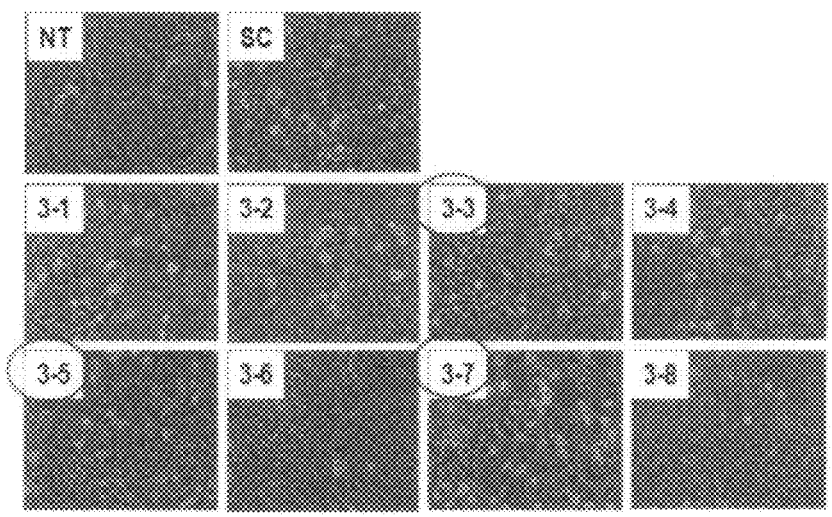
FIG. 2 is a photograph showing the growth states of the lung cancer cells treated with and without the siRNAs suppressive of the expression of FLJ25416.

FIGS. 1 and 2 show the down-regulation of the siRNAs against the expression of FLJ25416 at the post-transcriptional level in the human lung cancer cell line A549. FIG. 1 is a photograph after electrophoresis was performed, showing expression levels of the FLJ25416 transcript. FIG. 2 is a photograph showing growth states of the cells treated with and without the siRNA. In FIGS. 1 and 2, NT stands for a control which was not treated with siRNA, SC for a negative control treated with siScram, and 3-1 to 3-8 for groups treated respectively with 3-1 to 3-8 complexes. In addition, "GAPDH" means a glyceraldehyde 3-phosphate dehydrogenase gene set forth as a standard gene to normalize the difference in gene expression between the test groups. In the non-treated control (NT), the expression of the FLI25416 transcript was observed. The negative control (SC), which was treated with scrambled siRNA, showed no difference in the expression of FFLJ25416 from the control (NT). Various down-regulation effects were observed in the groups treated with the complexes of Examples 3-1 to 3-8, compared to the control. A significant decrease in the expression level of FLJ25416 was observed from the groups treated with the complex of Example 3-3 or 3-7 (FIG. 1). In addition, complexes of Examples 3-3, 3-5 and 3-7 showed inhibitory activity against the growth of the cancer cells (FIG. 2).

Example 5

RT-PCR Assay for Inhibitory Effect of the siRNA on Expression of FLJ25416 Transcript According to siRNA Concentration

Figure 3:
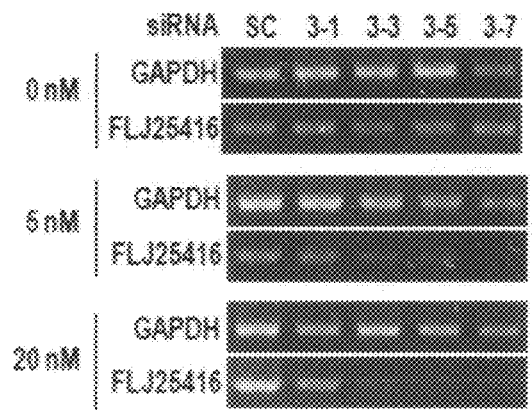
FIG. 3 is a photograph after electrophoresis was performed, showing expression levels of the FLJ25416 transcript upon treatment with the compositions of the present invention at different concentrations.

The same procedure as in Example 4 was repeated with the exception that the final concentrations of the siRNAs in the culture medium were adjusted to 5 nM and 20 nM and the cells were incubated for 48 hours at 37° C. in a $CO_2$ incubator. The results are shown in FIG. 3. FIG. 3 is a photograph after electrophoresis was performed, showing expression levels of the FLJ25416 transcript upon treatment with the complexes of Examples 3-1, 3-3 and 3-7 at different concentrations. In FIG. 3, 0 nM stands for groups treated with no test substances, SC for a negative control treated with scrambled siRNA, and GAPDH for a glyceraldehyde 3-phosphate dehydrogenase gene set forth as a standard gene to normalize the difference in gene expression between test groups. As can be seen, the complexes of 3-3, 3-5 and 3-7. elicited an mRNA knock-down effect even at 5 nM.

Example 6

Assay for Inhibitory Effect of the FLJ25416-Suppressing siRNA on Growth of Cancer Cells with Time

To evaluate the anti-cancer activity of the FLJ25416-suppressing siRNA, the growth of cancer cells was measured using an SRB (sulforhodamine B) assay. Detailed experimental, procedures are given infra.

The lung cancer cell line A549 (the Korean Cell Line Bank) was grown to 70% confluency. To the lung cancer cells, the complex compositions of siRNA and cationic liposome were added in such an amount that the final concentration of siRNA in the culture medium was 50 nM. Complexes were prepared slowly pipetting the liposome and the siRNA and leaving the mixture at room temperature for 20 min. They were plated into well plates containing the cells and incubated at 37° C. for 72 hours in a $CO_2$ incubator.

The cells were stained with SRB (sulforhodamine, Sigma Co.) and SRB-stained cells were counted to examine the inhibitory effect of the siRNAs on the cancer cells. The SRB assay was performed as follows. The cells grown on well plates were fixed with 4% formaldehyde at room temperature for 30 min, washed three times with distilled water and dried. The fixed cells were stained with 0.4% SRB (sulforhodamine B) (Sigma, S-9012) (1% acetic acid) at room temperature for 30 min and washed three times with 1% acetic acid. The stained cells was solubilized with 10 mM Tris-HCl (pH 10.5). The optical density was read at 540 nm to compare relative inhibitory activities of the siRNA against cell growth.

Figure 4:
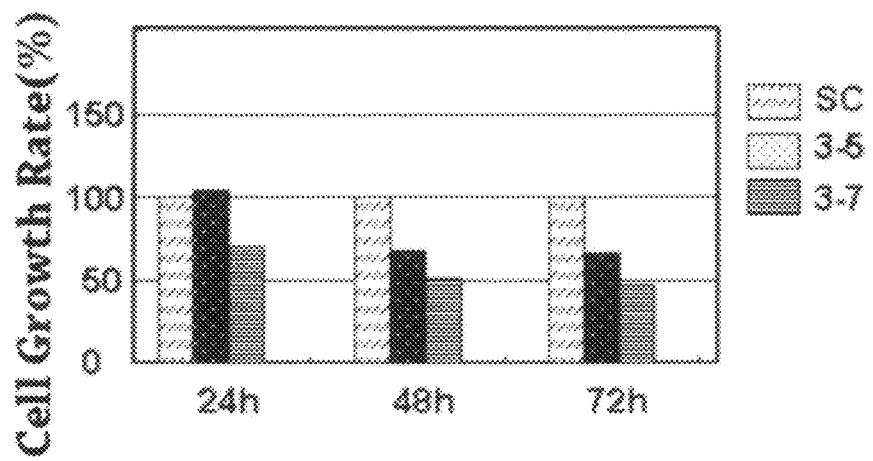
FIG. 4 is a graph showing the inhibitory activity of the FLJ25416-suppressing siRNAs against the growth of cancer cells with time.

The results are shown in FIG. 4. FIG. 4 is a graph showing the inhibitory activity of the FLJ25416-suppressing siRNAs against the growth of cancer cells with time. As can be seen in FIG. 4, the inhibition of the siRNAs against cancer cell growth increased with time. When treated with the 3-5 complex for 72 hours, the growth of the cancer cells was inhibited by 25.5%. The 3-7 complex was observed to inhibit the growth of the cancer cells by 28.4% within 24 hours, by 29.4% within 48 hours and by 37.8% within 72 hours. Hence, the most effective inhibitory activity was detected from the siRNA of Example 2-7:

Example 7

Preparation of Composition Comprising Modified siRNA and Cationic Liposome

The siRNA of Example 2-7, which was identified to have the greatest inhibitory activity against cancer cell growth, was structurally modified.

Structural modifications were preformed in Samchully Pharmaeuticals (Seoul, Korea) by (1) introducing a cholesterol group into the 5' terminus of the sense strand (cholesterol-conjugated siRNA), (2) introducing 2'-O-Me into all purine nucleosides on both the sense and the antisense strand (2'-O-Me siRNA), (3) introducing an amino group into the 5' terminus of the sense strand (amino modification), and (4) introducing 2'-F into all pyrimidine residues on the sense and antisense strands (2'-F siRNA). Sequences of the resulting modified siRNAs (7(1)~7(4)) from the siRNA of Example 2-7 are summarized in the following table.

|  | siRNA name | Sequence | 5'-3' |
|---|---|---|---|
| 7(1) | FLJ25416-7(chol) | Sense | Chol-CAG AAG ACA UCU GCA UGU UTT |
|  |  | Antisense | AAC AUG CAG AUC UCU UCU GTT |
| 7(2) | FLJ25416-7-O-Me | Sense | CmAmG mAmAmG mAmGmA UCU mGCmA UmGU UTT |
|  |  | Antisense | mAmAC mAUmG CmAmG mAUC UCU UCU mGTT |
| 7(3) | FLJ25416-7(amino) | Sense | NH2(CH2)6-CAG AAG AGA UCU GCA UGU UTT |
|  |  | Antisense | AAC AUG CAG AUC UCU UCU GTT |
| 7(4) | FLJ25416-7-F | Sense | fCAG AAG AGA fUfCfU GfCA fUGfU fUTT |
|  |  | Antisense | AAfC AfUG fCAG AfUfC fUfCfU fUfCfU GTT |

Chol: cholesterol,
mN: 2'-OMe,
fN: 2'-F,
N: A, G, C or U

Complex compositions (7-1~7-4) comprising the modified siRNAs in combination with cationic liposome were prepared in the same manner as in Example 3.

Example 8

In Vitro Effect of Modified siRNA

The compositions of Examples 7-1~7-4 comprising the modified siRNAs and the composition of Example 3-7 comprising the siRNA of Example 2-7 were added in such an amount to the uterine cancer cell line HeLa (purchased from the Korea Research Institute of Bioscience and Biotechnology (KRIBB)) that the final concentrations of each of the siRNAs were 5 nM. After induction of transfection, the cells were observed. For comparison, the composition comprising scrambled siRNA, prepared in Example 3, was used in the same manner.

Figure 5:
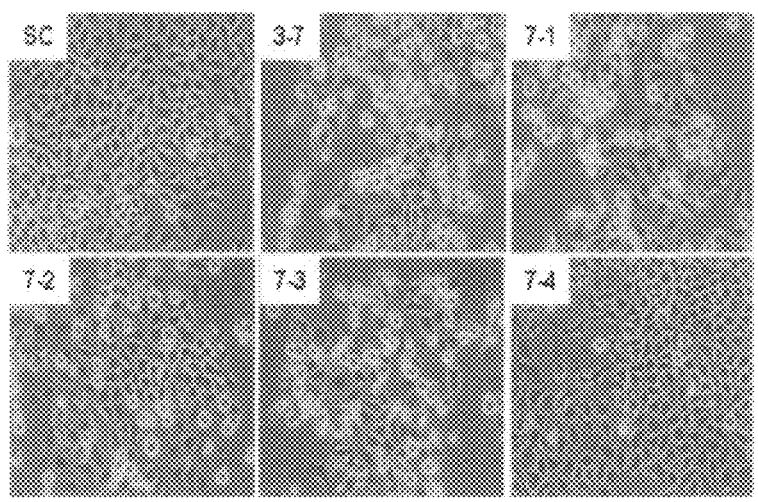
FIG. 5 shows inhibitory effects of the modified siRNAs of the present invention on the growth of the uterine cancer cells.

The result is given in FIG. 5. FIG. 5 shows inhibitory effects of the modified siRNAs on the growth of the uterine cancer cells. As can be seen in FIG. 5, the modified siRNAs induced the death in the cancer cells. That is, the siRNAs modified by amino modification, cholesterol conjugation or fluorine introduction effectively inhibited the growth of the cancer cells.

In addition, the inhibitory effect of the concentration modified siRNAs on cell growth was measured as follows. The compositions comprising the siRNAs (Examples 7-1 to 7-3), and the composition (Example 3-7) comprising the siRNA of Example 2-7 were added to the lung cancer cell line (A549) and the uterine cancer cell line (HeLa) in such an amount that the concentration of each of the siRNAs was 5 nM. An SRB (sulforhodamine B) assay was performed to measure the inhibitory activity 72 hours after the transfection. The cells were stained with SRB (sulforhodamine, Sigma Co.) and assayed for ability to inhibit the growth of cancer cells in the same manner as in Example 6.

Figure 6:
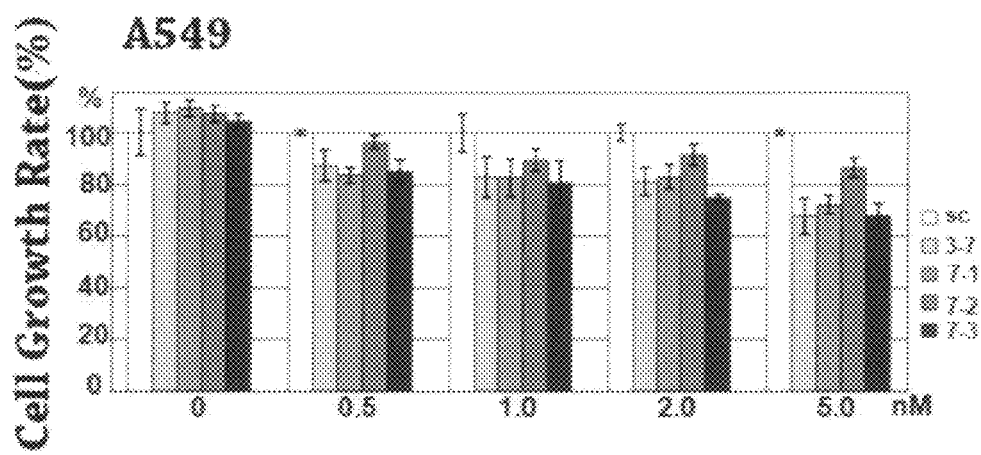
FIG. 6 is a graph showing inhibitory effects of the modified siRNAs at various concentrations on the lung cancer cell line transfected with the siRNAs.
Figure 7:
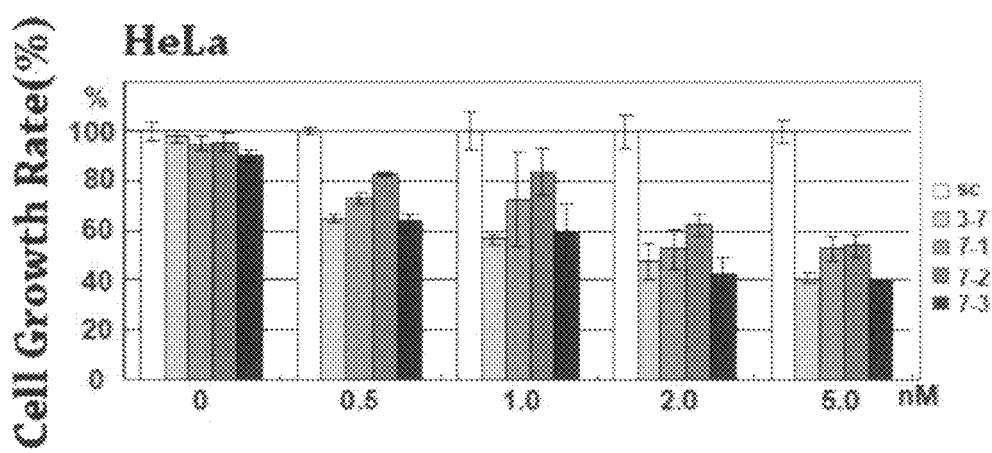
FIG. 7 is a graph showing inhibitory effects of the modified siRNAs at various concentrations on the uterine cervical cancer cell line transfected with the siRNAs.

The results are shown in FIGS. 6 and 7. FIGS. 6 and 7 are graphs showing the inhibitory effects of the modified siRNAs at various concentrations on the lung cancer cell line (A549) and the uterine cancer cell line (HeLa), respectively. In these figures, 'SC' stands for a control treated with scrambled siRNA.

As is understood from the data, the modified siRNAs inhibited the growth of the cancer cell lines in a dose-dependent manner and were effective even at a concentration of as low as 0.5 nM. Particularly, the composition comprising the siRNA modified by amino modification (7-3) exhibited an excellent anticancer effect.

Example 9

Confirmation of Inhibitory Effect of the Modified siRNAs on Expression of FLJ25416

The modified siRNAs were assayed for inhibitory activity against the expression of FLJ25416 in cancer and normal cells as described below.

Using the compositions (siRNA 0.5 nM) prepared in the same manner as in Example 7-3, transfection was performed into the normal cell line (WI38; ATCC (American Type Culture Collection). #CCL-75) and the uterine cancer cell line (HeLa). Their FLJ25416 mRNA levels were measured by Real-time PCR.

Real time PCR was performed using the SensiMix One-Step Kit (QT205-01), Quantace, according to the manufacturer's instruction. In this real-time PCR, 5'-gtgaccaagcacttc-gagttt-3' and 5'-gtgaccaagcacttcgagtt-3' were used as N- and C-terminal primers, respectively.

Figure 8:
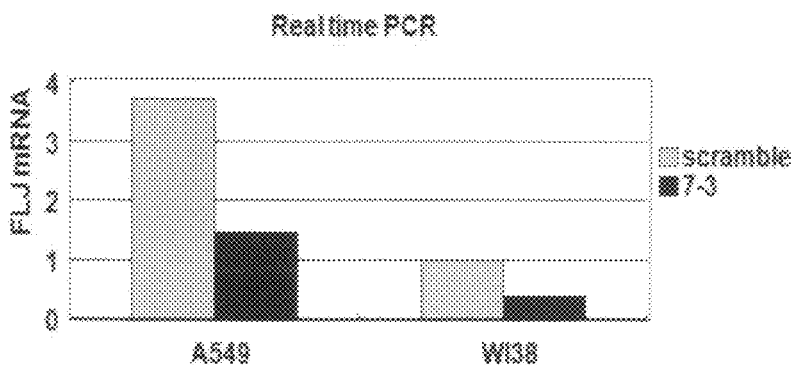
FIG. 8 is a graph showing the inhibitory activity of the modified siRNA against the expression of FLJ25416 in cancer and normal cell lines.

The results are shown in FIG. 8. FIG. 8 is a graph showing the inhibitory activity of the modified siRNA against the expression of FLJ25416 in cancer and normal cell lines. In this graph, "scramble" means a scrambled siRNA-treated group. The y-axis of FIG. 8 is the relative level of FLJ25416 mRNA which are normalized to the control GAPDH mRNA level in siRNA-treated cells.

As can be seen in FIG. 8, the modified siRNA suppressed the expression of FLJ25416 in both the normal and cancer cell lines.

Example 10

Inhibitory Effect of FLJ25416-Suppressing siRNA on Cell Growth

To examine the inhibitory effect of the modified siRNA on the growth of cancer and normal cell lines, cells were treated with siRNA in the same manner as in Example 4 and subjected to SRB assay as follows. The modified siRNA was used at concentrations of 0.1, 0.25 and 0.5 nM for the lung cancer cell line and at concentrations of 10, 20 and 50 nM for the normal cell line to measure inhibition against cell growth according to the amount of siRNA.

The cells were stained with SRB (sulforhodamine, Sigma Co.) and SRB-stained cells were counted to examine the inhibitory effect of the siRNAs on the cancer cells.

Figure 9:
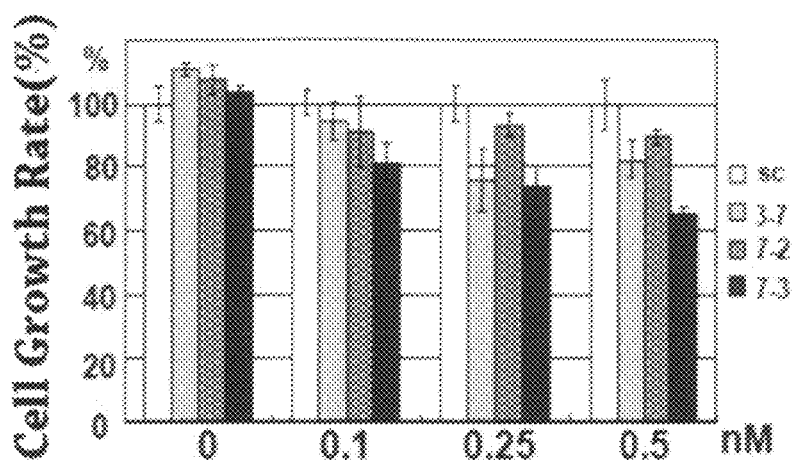
FIG. 9 is a graph showing growth rates of lung cancer cells treated with the predetermined concentrations of the siRNAs.
Figure 10:
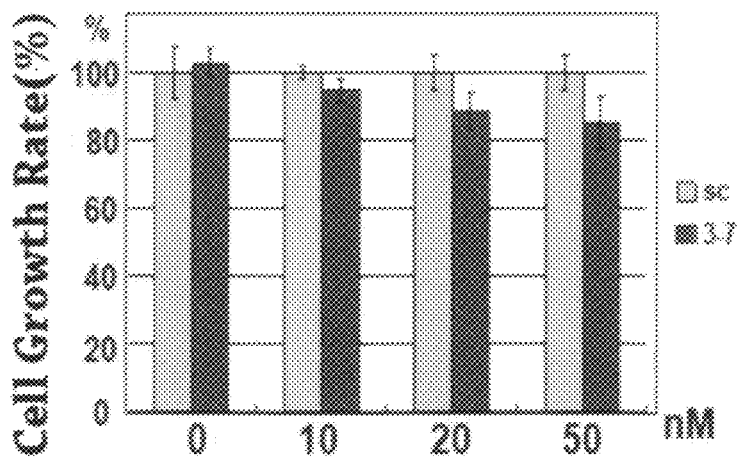
FIG. 10 is a graph showing growth rates of normal cells treated with the predetermined concentrations of the siRNAs.

The results are shown in FIGS. 9 and 10. FIGS. 9 and 10 are graphs showing growth rates of cancer cells (A549) and normal cells (WI38) treated with the predetermined concentrations of the siRNAs. In the graphs, SC means a scrambled siRNA-treated group.

As can be seen, the growth of normal cells was decreased by as high as 15% when they were treated with 20 nM and 50 nM of siRNA. In contrast, a higher inhibitory effect was observed even at a low concentration (0.25 nM) in the cancer cells. Particularly, the siRNA-amino, prepared by introducing an amino group, was found to effectively inhibit the growth of cancer cell line even when it was used at a concentration of 0.1 nM.

As is understood from the data of examples 9 and 10, the down-regulation of gene expression increased the inhibition of cell growth in cancer cells than in normal cells, indicating that the siRNAs suppressive of the expression of FLJ25416 selectively inhibit the growth of cancer cells. The siRNA modified by amino modification (Example 7-3) was observed to exhibit higher anticancer activity.

Example 11

Cell Death of Cancer Cells Induced by the Modified siRNA

The lung cancer cell line (A549; the Korean Cell Line Bank) and the uterine cancer cell line (HeLa: KRIBB) were treated with the compositions of Examples 3-7 and 7-3 and the siScram composition, each 5 nM of siRNA, followed by FACS (Fluorescence Activated Cell Sorter) analysis to monitor cell cycles over time.

For this, first, the lung cancer cell line and the uterine cancer cell line were transfected with 5 nM of each siRNA (scram, 3-7 and 7-3) and DNA stained with PI (propidium iodide) at predetermined times after the transfection, followed by monitoring cell cycles by DNA content analysis with FACScan™ (Becton, Dickinson and company).

Figure 11:
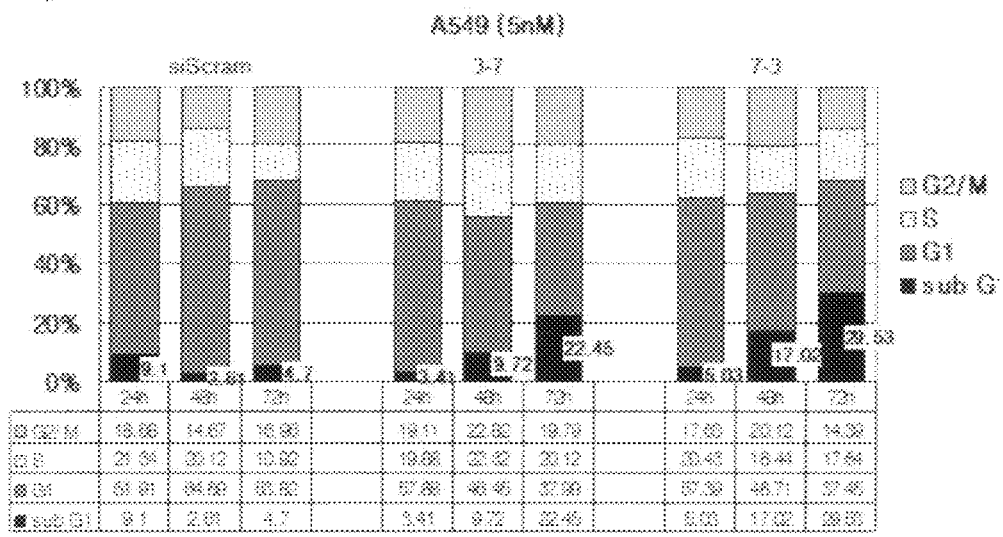
FIG. 11 is a graph showing changes in cells cycle with time in the lung cancer cell line treated with the siRNA of the present invention.
Figure 12:
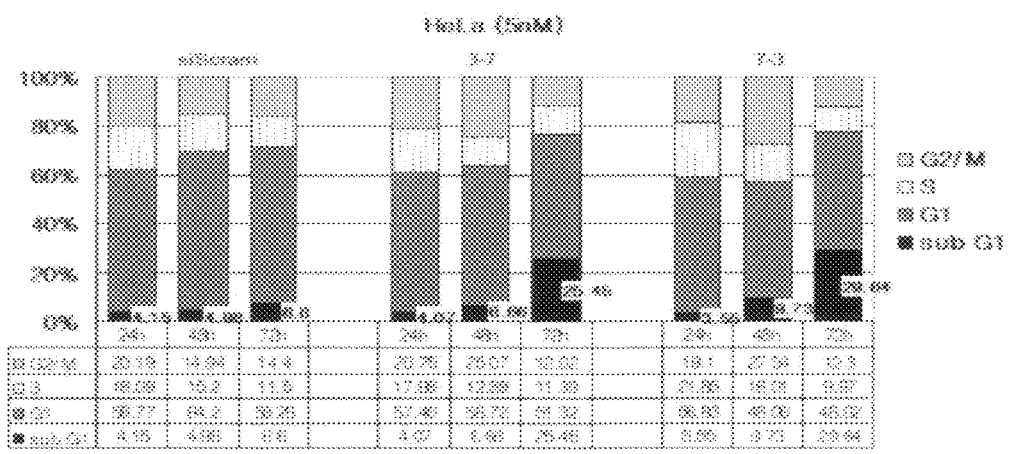
FIG. 12 is a graph showing changes in cells cycle with time in uterine cervical cells treated with the siRNA of the present invention.

The results are shown in FIGS. 11 and 12, which are graphs showing changes in the cell cycle with time in the lung cancer cell line (A549) and the uterine cancer cell line (HeLa).

In FIGS. 11 and 12, G2/M, S, G1 and sub G1represent the phases constituting the cell cycle, and sub G1 accounts for the cell death phase. A greater percentage of sub G1 means a higher proportion of cells that undergo cell death.

As is understood from the data, the percentage of sub-G1 increased with time in the cells treated with the compositions of Examples 3-7 and 7-3 (modified siRNA), indicating the cells undergoing cell death increased with time. In addition, a larger percentage of sub-G1 was induced in cells treated with the composition comprising the siRNA of amino modification (Example 7-3) than in those treated with the composition comprising the non-modified siRNA, suggesting that the modified siRNA has potent anticancer activity.

Example 12

In vivo Assay for Anticancer Activity of FLJ25416-Suppressing siRNA

Figure 13:
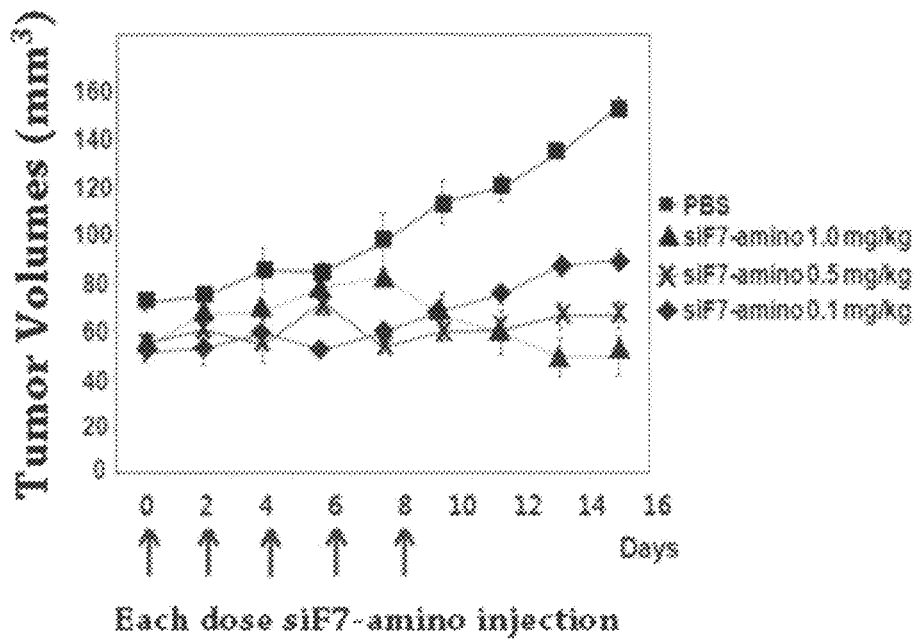
FIGS. 13 and 14 are graphs showing tumor volumes over time in the mice administered with the composition comprising the siRNA of the present invention.
Figure 14:
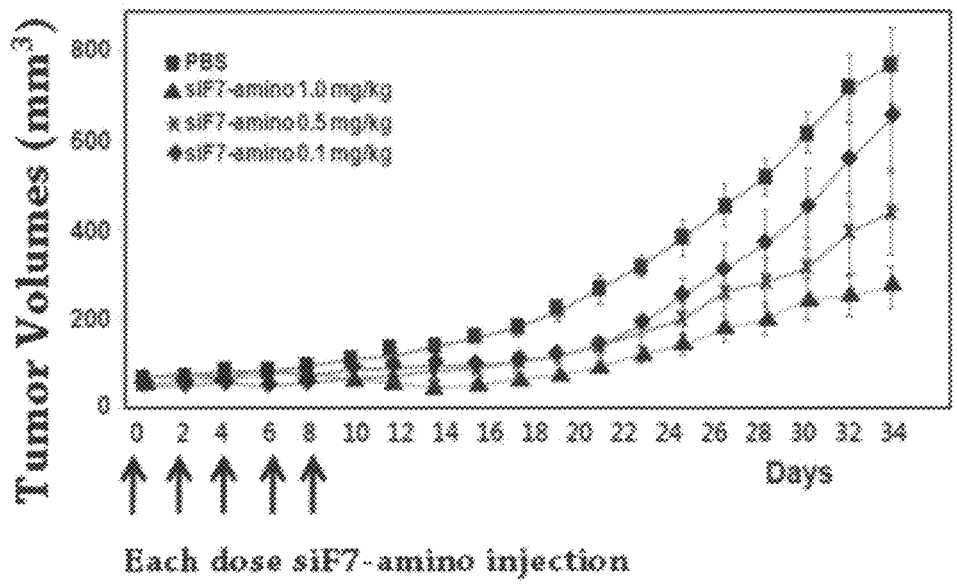

To examine in vivo anticancer activity of the siRNA suppressive of the expression of FLJ25416, nude mice with A549 lung cancer were experimented on as follows. A suspension of $5 \times 10^6$ lung cancer cells (A549) in 100 µL of Hanks' balanced salt solution (HBSS) was subcutaneously injected into the abdominal wall of nude mice 7~8 weeks old (Orient). On 10~14 days after tumor cell implantation when the tumor grew about 50-70 mm$^3$ in volume, the nude mice were divided four groups one of which was used as a negative control, the remaining three groups were administered five times with the siRNA by intratumoral injection at a dose of 0.1 mg/kg, 0.5 mg/kg and 1.0 mg/kg, respectively, every two days. The volume of the tumor was measured every two days. For the negative control, PBS (phosphate buffered saline) was administered. The results are shown in FIGS. 13 and 14 which are graphs showing tumor volumes over time in the mice administered with the composition of Example 7-3. In FIGS. 13 and 14, "PBS" and "siF7-amino" mean nude mouse groups administered with PBS and the composition of Example 7-3, respectively. The tumors were not grown in the group administered with siRNA of Example 7(3) at a dose of 0.5 mg/kg until day 16 and became smaller in the group administered at a dose of 1.0 mg/kg on day 15. Further, the siRNA was found to inhibit the growth of the tumor in a dose-dependent manner as observed until 34 days. The tumor volume was reduced by 28.1% at a dose of 0.1 mg/kg, by 56.5% at a dose of 0.5 mg/kg and by 69.6% at a dose of 1.0 mg/kg. Therefore, the siRNAs of the present invention were found to have potent anticancer activity.

Example 13

Synthesis of Antisense RNA

Antisense RNAs (13-1~13-3) were synthesized using the same procedure as the antisense strands of Example 2 with the exception that the RNAs had nucleotide sequences of SEQ ID NOS: 14, 18 and 22 of Table 2, respectively.

Example 14

Design and Synthesis of DNA Coding for shRNA

DNA molecules which code respectively for shRNAs having a set of nucleotide sequences of SEQ ID NOS: 13 and 14, a set of nucleotide sequences of SEQ ID NOS: 17 and 18, and a set of nucleotide sequences of SEQ ID NOS: 21 and 22, said nucleotide sequences in each set being connected with each other via a loop sequence, were designed and constructed.

In detail, a DNA duplex which was comprised of the DNA sequence of SEQ ID NO: 28 corresponding to the RNA sequences of SEQ ID NOS: 13 and 14 with a loop sequence (GAGCTC) intercalated therebetween, and the complementary DNA sequence thereof was designed and synthesized. Likewise, other DNA duplexes was designed and synthesized which were comprised of the DNA sequence of SEQ ID NO: 29 and its complementary sequence, and the DNA sequence of SEQ ID NO: 30 and its complementary sequence, which correspond respectively to the RNA sequences of SEQ ID NOS: 17 and 18 and SEQ ID NOS: 21 and 22, with a loop sequence (GAGCTC) intercalated between the RNA sequence in each DNA strand (Bioneer, Korea).

Adenovirus carrying each of the DNA duplexes was infected into cells to induce RNAi (Korean. Patent. Laid-Open Publication No. 10-2009-0060183).

Industrial Applicability

Having the ability to suppress the expression of FLJ25416, common to cancer cells, by RNAi, the siRNA, the antisense RNA and/or the shRNA molecules, complementary to the FLJ25416 transcript (mRNA), of the present invention can induce cancer cells to undergo cell death, and thus can be applied to an anticancer composition.

The invention claimed is:

1. A pharmaceutical composition for therapy of cancer, comprising a small interfering ribonucleic acid (siRNA) molecule, wherein:
   the siRNA molecule suppresses expression of FLJ25416 within cells by complementarily binding to a base sequence of an FLJ25416 transcript (mRNA) represented by SEQ ID NO: 5 or SEQ ID NO: 7; and
   the siRNA molecule has the sense sequence set forth as SEQ ID NO: 21 and the antisense sequence set forth as SEQ ID NO: 22.

2. The pharmaceutical composition of claim 1, wherein the siRNA molecule has a modification selected from among 2'-O-methyl modification, 2'-F modification, amino modification, cholesterol conjugation, and a combination thereof.

3. The pharmaceutical composition of claim 1, further comprising a nucleic acid delivery system.

4. The pharmaceutical composition of claim 3, wherein the nucleic acid delivery system is selected from among a cationic liposome and a cationic polymer.

5. The pharmaceutical composition of claim 1, wherein the cancer is selected from among lung cancer, uterine cervical cancer, colorectal cancer, stomach cancer and liver cancer.

6. An siRNA molecule, which suppresses expression of FLJ25416, wherein the siRNA molecule has the sense sequence set forth as SEQ ID NO: 21 and the antisense sequence set forth as SEQ ID NO: 22.

* * * * *

UNITED STATES PATENT AND TRADEMARK OFFICE
CERTIFICATE OF CORRECTION

| | | |
|---|---|---|
| PATENT NO. | : 8,846,630 B2 | Page 1 of 1 |
| APPLICATION NO. | : 13/512583 | |
| DATED | : September 30, 2014 | |
| INVENTOR(S) | : Misun Won et al. | |

It is certified that error appears in the above-identified patent and that said Letters Patent is hereby corrected as shown below:

IN THE TITLE PAGES:

Item (75) Inventors:

page 1, lines 10-12, replace "Eun Young Song, Seoul (KR); Seok Hoon Song, legal representative, Seoul (KR);" with —Eun Young Song, Seoul (KR);—.

page 1, lines 14-15, replace "Kyeong-Eun Jung, Anyang-si (KR)" with —Kyeong-Eun Jung, Gyeonggi-do (KR)—.

Signed and Sealed this
Seventeenth Day of February, 2015

Michelle K. Lee
*Deputy Director of the United States Patent and Trademark Office*